United States Patent
Lunner et al.

(10) Patent No.: US 9,635,469 B2
(45) Date of Patent: Apr. 25, 2017

(54) AUTOMATIC REAL-TIME HEARING AID FITTING BASED ON AUDITORY EVOKED POTENTIALS

(71) Applicant: Oticon A/S, Smørum (DK)

(72) Inventors: Thomas Lunner, Smørum (DK); Tobias Neher, Oldenburg (DE)

(73) Assignee: OTICON A/S, Smorum (DK)

( * ) Notice: Subject to any disclaimer, the term of this patent is extended or adjusted under 35 U.S.C. 154(b) by 525 days.

(21) Appl. No.: 13/651,032

(22) Filed: Oct. 12, 2012

(65) Prior Publication Data

US 2013/0101128 A1    Apr. 25, 2013

Related U.S. Application Data

(60) Provisional application No. 61/547,079, filed on Oct. 14, 2011.

(30) Foreign Application Priority Data

Oct. 14, 2011   (EP) .................................... 11185225

(51) Int. Cl.
H04R 29/00   (2006.01)
H04R 25/00   (2006.01)
(Continued)

(52) U.S. Cl.
CPC ......... *H04R 25/30* (2013.01); *A61B 5/04845* (2013.01); *A61B 5/121* (2013.01);
(Continued)

(58) Field of Classification Search
None
See application file for complete search history.

(56) References Cited

U.S. PATENT DOCUMENTS 6,574,513 B1   6/2003   Collura et al.
7,035,745 B2   4/2006   Stürzebecher
(Continued)

FOREIGN PATENT DOCUMENTS

EP   1 073 314 A1   1/2001
EP   1 295 509 A    3/2003
(Continued)

OTHER PUBLICATIONS

English Translation of EP1073314, Jan. 31, 2001.*
(Continued)

*Primary Examiner* — Joseph Saunders, Jr.
*Assistant Examiner* — James Mooney
(74) *Attorney, Agent, or Firm* — Buchanan Ingersoll & Rooney P.C.

(57) ABSTRACT

A hearing aid includes at least one electrode located at a surface of a housing of the hearing aid to allow the electrodes to contact the skin of a user during use of the hearing aid, at least one electrode being adapted to pick up a low voltage signal from the user's brain, an amplifier unit operationally connected to the electrode(s) and adapted for amplifying the low voltage signal(s) to provide amplified brain signal(s), and a signal processing unit adapted to process the amplified brain signal(s) to provide a processed brain signal as well as to apply a time and frequency dependent gain to an input audio signal and to provide a processed audio output signal. Also a method of operating a hearing aid and a hearing aid system.

20 Claims, 6 Drawing Sheets

(51) Int. Cl.
  *A61B 5/0484* (2006.01)
  *A61B 5/12* (2006.01)
  *A61B 5/00* (2006.01)
  *G06F 3/01* (2006.01)

(52) U.S. Cl.
  CPC ........... *A61B 5/6815* (2013.01); *H04R 25/70* (2013.01); *G06F 3/015* (2013.01); *H04R 25/552* (2013.01); *H04R 25/554* (2013.01); *H04R 25/558* (2013.01)

(56) References Cited

U.S. PATENT DOCUMENTS

| | | |
|---|---|---|
| 2002/0028991 A1 | 3/2002 | Thompson |
| 2004/0185773 A1 | 9/2004 | Gerber et al. |
| 2008/0033317 A1 | 2/2008 | Elberling |
| 2010/0067723 A1 | 3/2010 | Bergmann et al. |
| 2011/0059696 A1 | 3/2011 | Rasmussen et al. |
| 2011/0188664 A1 | 8/2011 | Morikawa et al. |
| 2011/0200217 A1* | 8/2011 | Gurin ............................. 381/320 |
| 2012/0165695 A1 | 6/2012 | Kidmose et al. |
| 2012/0177233 A1* | 7/2012 | Kidmose et al. ............. 381/314 |
| 2012/0219159 A1* | 8/2012 | Burk et al. ...................... 381/60 |
| 2014/0193010 A1* | 7/2014 | Goll .................... H04R 25/453 381/318 |

FOREIGN PATENT DOCUMENTS

| | | |
|---|---|---|
| EP | 1 460 769 A1 | 9/2004 |
| EP | 1 981 253 A1 | 10/2008 |
| EP | 2 200 347 A2 | 6/2010 |
| WO | WO 01/05207 A2 | 1/2001 |
| WO | WO 2006/003172 A1 | 1/2006 |
| WO | WO 2009/135872 A1 | 11/2009 |
| WO | WO 2010/149157 A1 | 12/2010 |
| WO | WO 2011/006681 A1 | 1/2011 |
| WO | WO2013017169 * | 8/2011 |

OTHER PUBLICATIONS

European Search Report issued Apr. 23, 2012, in corresponding EP 11185225.7.
P. Sörqvist et al., "Working Memory Capacity and Visual-Verbal Cognitive Load Modulate Auditory-Sensory Gating in the Brainstem: Towards a Unified View of Attention", Manuscript accepted for publication in Journal of Cognitive Neuroscience, 28 pages.
http://en.wikipedia.org/wiki/Auditory_evoked_potential (9 pages).
http://en.wikipedia.org/wiki/Auditory_brainstem_response (11 pages).
E. Skoe et al., "Auditory Brain Stem Response to Complex Sounds: A Tutorial", Ear & Hearing, 2010, pp. 302-324, vol. 31, No. 3.
http://en.wikipedia.org/wiki/Event-related_potential (7 pages).
Office Action issued on Aug. 8, 2016, by the European Patent Office in the corresponding European Patent Application No. 11 185 225.7-1910. (6 pages).

* cited by examiner

AUTOMATIC REAL-TIME HEARING AID FITTING BASED ON AUDITORY EVOKED POTENTIALS

CROSS-REFERENCE TO RELATED APPLICATIONS

This application claims priority under 35 U.S.C. §119 to European Patent Application No. 11185225.7 filed in Europe on Oct. 14, 2011, and U.S. Provisional Patent Application No. 61/547,079, filed on Oct. 14, 2011, the contents of both of which are hereby incorporated by reference in their entirety.

TECHNICAL FIELD

The present application relates to hearing aids, and to the monitoring of auditory evoked potentials (AEP). The disclosure relates specifically to a hearing aid comprising means for picking up and analysing auditory evoked potentials, e.g. an auditory brainstem response (ABR). The application furthermore relates to a method of operating a hearing aid and to the use of a hearing aid. The application further relates to a data processing system comprising a processor and program code means for causing the processor to perform at least some of the steps of the method.

The disclosure may e.g. be useful in hearing aids or hearing aid systems where a continuous evaluation of a user's hearing thresholds is needed.

BACKGROUND

Fitting of a hearing aid to a particular person's hearing impairment generally requires knowledge of clinically measured hearing thresholds for the person in question. The auditory brainstem response (ABR) can be used as an objective estimate of audiometric hearing thresholds (e.g. [Stürzebecher et al., 2006]). ABR signals are traditionally measured by surface electrodes mounted on the head with one electrode at the vertex or in the middle of the forehead, one behind the ear on the mastoid or on the earlobe, and one ground electrode on the opposite side of the head. Future hearing aids may, however, include electrodes on the surface of the hearing aid shell facing the ear canal to record electric brain wave signals such as an electroencephalogram (EEG) (cf. e.g. [Lunner, 2010]).

A portable EEG monitoring apparatus is described in [Kidmose and Westermann, 2010]. A hearing aid comprising electrodes for detecting electrical signals such as brain waves is described in [Kidmose and Mandic, 2011]. The design of stimuli for a system for the recordal of an auditory brainstem response (ABR) of a person is e.g. described in WO 2006/003172 A1.

SUMMARY

Auditory evoked potentials (AEPs) are a subclass of event-related potentials (ERP)s, such as auditory brainstem response (ABR). ERPs are brain responses that are time-locked to some "event", such as a sensory stimulus, a mental event (such as recognition of a target stimulus), or the omission of a stimulus. For AEPs, the "event" is a sound. AEPs (and ERPs) are very small electrical voltage potentials originating from the brain recorded from the scalp in response to an auditory stimulus, such as different tones, speech sounds, etc.

The analysis of measured AEPs for a person can be used to estimate audiometric hearing thresholds (HTL) of that person. A fitting algorithm can be executed in the hearing aid using the estimated hearing thresholds as inputs to determine an appropriate frequency dependent gain for the user wearing the hearing aid.

In an aspect of the present disclosure, it is proposed to send out auditory test signals (e.g. chirps, clicks, or narrow-band signals such as tones making auditory steady state response, ASSR) from a hearing aid receiver under daily use and with the hearing aid equipped with electrodes to electrically measure brain signals.

It is further proposed to use auditory models to continuously being able to present an auditory test signal that does not disturb the user of the hearing aid. The auditory test signals are thus presented through the hearing aid under daily life use in a way that the test signals are partly or fully inaudible (via e.g. a loudness masking model). The point is that through the hearing aid in daily use, extremely many test signals may be presented since measuring time is not really an issue compared to a clinical AEP (e.g. ABR) testing situation, and therefore an accurate estimation of the AEP response can be obtained. The AEP test signal and the environmental signal can be, at least to a first approximation, seen as independent signals, and therefore will long term averaging of the recorded electric brain waves make a good estimate of an AEP and hence make an estimate of the acoustic hearing thresholds. Thereby no clinically measured hearing thresholds are required, since the hearing thresholds are estimated from the auditory brain response.

An object of the present application is to provide a hearing aid capable of monitoring a user's hearing ability over time.

Objects of the application are achieved by the invention described in the accompanying claims and as described in the following.

A Hearing Aid:

In an aspect of the present application, an object of the application is achieved by a hearing aid comprising an ear part adapted for being mounted fully or partially at an ear or in an ear canal of a user, the ear part comprising
a housing,
at least one electrode located at a surface of said housing to allow said electrodes to contact the skin of a user when said ear part is operationally mounted on the user, the at least one electrode being adapted to pick up a low voltage electric signal from the user's brain, an amplifier unit operationally connected to said electrode(s) and adapted for amplifying said low voltage electric signal(s) to provide amplified brain signal(s), an input transducer for providing an electric audio input signal, a signal processing unit, an output transducer for converting an electric output signal to an acoustic output sound, said signal processing unit being operationally connected
to said amplifier unit and adapted to process said amplified brain signal(s) to provide a processed brain signal,
to said input transducer and adapted to apply a time and frequency dependent gain to said electric audio input signal or a signal originating therefrom and to provide a processed audio output signal, and
to said output transducer allowing said processed audio output signal to be presented to the user as a processed acoustic signal, wherein the hearing aid further comprises a signal generator for generating an electric test signal specifically adapted to be used in an auditory evoked potential (AEP) measurement, the signal generator being operationally connected to said output transducer allowing said electric test signal to be converted to an auditory test stimulus for being presented to a user together with said processed acoustic signal during use of the hearing aid.

This has the advantage of providing a hearing aid wherein at least a part of the fitting process of a hearing aid to a particular user can be automated and/or continuously updated.

In an embodiment, the hearing aid comprises at least two electrodes. In an embodiment, the hearing aid comprises a reference electrode.

In an embodiment, the electric test signal is adapted to provide that the auditory test stimulus is masked and/or inaudible to the user. Such adaptation may e.g. be based on a model of the human auditory system, e.g. a loudness masking model. Psycho-acoustic models of the human auditory system are e.g. discussed in [Fastl & Zwicker, 2007], cf. e.g. chapter 4 on 'Masking', pages 61-110, and chapter 7.5 on 'Models for Just-Noticeable Variations', pages 194-202. An advantage thereof is that when the auditory test stimuli are partly or fully masked they will not compromise the normal daily use of the hearing aid.

In an embodiment, the signal processor is adapted to estimate the user's hearing thresholds based on said processed brain signals. This has the advantage that the hearing aid can be fully or partially self fitting. In an embodiment, the estimate of the user's hearing threshold is based on processed brain signals from low voltage electric signals picked up by the at least one electrode over a period of time, termed the measurement time. In an embodiment, the measurement time is longer than 8 hours, such as longer than one day, such as longer than one week, such as longer than one month.

In an embodiment, the auditory evoked potential is an auditory brainstem response. The auditory brainstem response is an auditory evoked potential extracted from ongoing electrical activity in the brain and recorded via electrodes placed on the scalp. AEP and ABR are e.g. described in Wikipedia [Wiki-AEP] and [Wiki-ABR], respectively.

In an embodiment, the auditory evoked potential is an auditory steady state response. Auditory Steady State Response (ASSR) is an auditory evoked potential, elicited with modulated tones that can be used to predict hearing sensitivity in patients of all ages. It is an electrophysiologic response to rapid auditory stimuli and creates a statistically valid estimated audiogram (evoked potential used to predict hearing thresholds for normal hearing individuals and those with hearing loss). The ASSR uses statistical measures to determine if and when a threshold is present and is a "cross-check" for verification purposes prior to arriving at a differential diagnosis [Wiki-ABR] (see e.g. U.S. Pat. No. 7,035,745 or [Stürzebecher et al., 2006]).

In the same way, a frequency specific hearing threshold level (HTL) estimate can be provided through ASSR.

With such estimate, where the ASSR (or ABR) signals have been presented through the hearing aid output and recorded using the ear electrodes, the frequency specific ASSR response provides an estimate of the hearing sensitivity as a function of frequency. Furthermore, these HTLs can then be used to apply conventional hearing threshold based prescription rules. In an embodiment, the signal processor is adapted to run a fitting algorithm, such as NAL-RP, NAL-NL2 (National Acoustic Laboratories, Australia), DSL (National Centre for Audiology, Ontario, Canada), ASA (American Seniors Association), VAC (Veterans Affairs Canada), etc. using said estimated hearing thresholds. The fitting algorithm uses the estimated hearing thresholds to determine the appropriate frequency dependent gain for the user. In an embodiment, the hearing aid is adapted to execute the fitting algorithm in real-time. In an embodiment, the hearing aid is adapted to execute the fitting algorithm automatically.

In certain cases where behavioral thresholds cannot be attained, ABR thresholds can be used for hearing aid fittings. New fitting formulas such as DSL v5.0 allow the user to base the settings in the hearing aid on the ABR thresholds. Correction factors do exist for converting ABR thresholds to behavioral thresholds. The Desired Sensation Level multistage input/output algorithm (DSLm[i/o]) is an electroacoustic fitting algorithm particularly aimed at children (National Centre for Audiology, Ontario, Canada).

So when the hearing aid records the AEP, e.g. ASSR, response during daily use for some time (e.g. a few days, e.g. at least 3-5 days) (without amplification or just minor amplification) the estimate of the ASSR response is accurate and the hearing aid can use the given prescription rule (NAL, DSL, etc.) to provide an individually prescribed amplification scheme (without having to measure and enter a clinically obtained audiogram).

AEP measurements may further be used to measure supra-threshold effects. Supra-threshold AEPs can help to determine whether the signal processing applied in a hearing aid is appropriate to make certain acoustic information not just audible but usable to the user. In other words, online supra-threshold AEP measurements may be used to steer the signal processing, e.g. it could be made more aggressive if the hearing loss worsens (as verified by means of objective hearing threshold measurements, for example), so that the important acoustic information still gets through.

One example of such supra-threshold measure is the measure of the ABR activity as is it is (without dedicated periodic acoustic stimuli). However, since it will not be based on repeated sound, it is difficult to use in this application. However, Frequency Following Response (FFR) may advantageously be used. It has been shown that trained musicians have a more distinct and pronounced FFR compared to untrained subjects. Hearing impaired subjects have a poorer FFR.

Frequency following response (FFR), also referred to as Frequency Following Potential (FFP), is an evoked response generated by continuous presentation of low-frequency tone stimuli. Unlike the Acoustic Brain Reflex (ABR), the FFR reflects sustained neural activity; integrated over a population of neural elements. It is phase locked to the individual cycles of the stimulus waveform and/or the envelope of the periodic stimuli.

The collection and analysis of auditory brainstem responses to complex sounds (cABR) may be used to track the systemic changes due to intervention (e.g. by the use of ordinary hearing aids) (cf. e.g. [Skoe & Kraus, 2010]). According to the present disclosure, the cABR generation and brainstem recording can be made through the electrode equipped hearing aids, where the hearing aid settings are changed in order to maximize the measured FFR response. This means that the compression settings and gain as a function of frequency are altered in the direction of increased FFR response.

In general, it has been assumed that the AEP, e.g. ABR, signals are objective in the sense that they are automatically (reflexively) generated by the person's perceptive system and not influenced by the person's will. This assumption is the basis of an independent determination of hearing thresholds from such measurements. It has, however, been indicated (c.f. e.g. [Sörqvist et al.; 2012?]) that also AEP, e.g. ABR, signals—under certain circumstances—may be sensitive to a person's will, and thus that such assumingly 'objective' measurements may be distorted. According to the present disclosure, however, due the relatively long measurement times (e.g. continuous measurement), such 'incidents' of non-reflexive action may be eliminated from influencing the results due to long term averaging of the AEP-signals or specific identification of such 'distorted' time segments and elimination from the calculation.

In an embodiment, the measuring time during which brain wave signals, e.g. AEP data (e.g. ABR data) are recorded and (possibly continuously) processed is longer (such as much longer) than a normal clinical AEP recording session. In an embodiment, the measuring time is longer than 8 hours, such as longer than one day, such as longer than one week, such as longer than one month.

In an embodiment, the measuring time is an accumulated measuring time, in case the measurements have been interrupted (and/or that time segments of the data have been eliminated).

In an embodiment, a measurement time comprises a large number of recorded AEP-responses, e.g. more than one hundred or more than one thousand or more than ten thousand responses. In an embodiment, the complex values of the large number of recorded AEP-responses are added in magnitude and phase (and possibly averaged).

In general, due to long measurement times, the ambient real world sounds will be cancelled/averaged out of the averaging process since the only repeated response is the evoked potential/event related potential. In an embodiment, however, the hearing aid comprises one or more filters, such as one or more variable filters, adapted to filter the low voltage electric signal(s) (as picked up by the electrode(s)) and/or the amplified brain signal(s) before being further processed to estimate the user's hearing thresholds. In an embodiment, the hearing aid is adapted to use or NOT use the voltages or data from the electrodes depending on an indication of the user's current environment, e.g. acoustic environment, and/or cognitive load, or e.g. depending on an input from the user.

In an embodiment, the hearing aid comprises a number of hearing aid programs adapted for providing a signal processing of the input audio signal in various specific acoustic environments or situations (e.g. speech in noise, speech in silence, live music, streamed music or sound, telephone conversation, silence, 'cocktail party', etc.). In an embodiment, the hearing aid comprises different transfer functions for the variable filter(s) corresponding to the different hearing aid programs, so that a transfer function corresponding to a particular acoustic situation is applied to the variable filter, when the program for that acoustic situation is used in the hearing aid. Alternatively or additionally, the hearing aid may comprise one or more detectors for identifying the acoustic environment. In an embodiment, the hearing aid is adapted to apply a transfer function corresponding to a particular acoustic situation to the variable filter depending on the acoustic situation indicated by said detector(s).

In an embodiment, the hearing aid is adapted to provide that the filtering of the low voltage electric signal(s) and/or the amplified brain signal(s) is dependent on an estimate of the current cognitive load of the user. A hearing aid wherein the processing of an audio input is adapted in dependence of an estimate the present cognitive load of the user is e.g. discussed in [Lunner, 2010], which is hereby incorporated by reference.

In an embodiment, the hearing aid comprises a user interface adapted for allowing a user to activate or deactivate a specific mode (e.g. termed an AEP- or ABR-mode) where the voltages or data from the electrodes are recorded for further processing to determine an estimate of the user's hearing thresholds. In an embodiment, the user interface is adapted to allow a user to start an estimation of new hearing thresholds (ignoring previously recorded values).

Furthermore, such online estimated ABR response can be used to monitor (also in a relatively long-term perspective, i.e. over days, or months) whether the hearing thresholds deteriorate (i.e. increase) over time (and if so, to possibly inform the user thereof).

In an embodiment, the hearing aid comprises a memory for logging values of said estimated hearing thresholds of the user over time. In an embodiment, values of the estimated hearing thresholds are stored with a predefined log frequency, e.g. at least once every hour, such as at least once every day.

In an embodiment, the signal processing unit is adapted to determine whether said estimated hearing thresholds or a hearing threshold measure derived therefrom change over time, e.g. by determining corresponding rates of change (e.g. a rate of increase or decrease).

ERPs (including AEPs) can be reliably measured using electroencephalography (EEG), a procedure that measures electrical activity of the brain through the skull and scalp. As the EEG reflects thousands of simultaneously ongoing brain processes, the brain response to a single stimulus or event of interest is not usually visible in the EEG recording of a single trial. To see the brain response to the stimulus, the experimenter must conduct many trials (100 or more) and average the results together, causing random brain activity to be averaged out and the relevant ERP to remain. While evoked potentials reflect the processing of the physical stimulus, event-related potentials are caused by the "higher" processes that might involve memory, expectation, attention, or changes in the mental state, among others (cf. [Wiki-ERP]).

Such (automatic) real time AEP (e.g. ABR) may be used for temporal fitting, meaning that the hearing aid initially provided to the user may comprise no or little amplification. Over time, when the AEP response grows through averaging, the hearing threshold estimates become more and more valid, and reliable values for such threshold estimates emerge (possibly replacing previous clinically measured hearing thresholds). Thereby automatic hearing threshold based prescription of a hearing aid through 'online AEP' may be implemented.

In an embodiment, the signal processor is adapted to modify the presently used (time and) frequency dependent gains of the hearing aid, based on said estimated hearing thresholds. In an embodiment, such modification of the intended frequency dependent gain values is performed according to a predefined scheme, e.g. with a predefined update frequency, and/or if said currently estimated hearing thresholds deviate with a predefined amount from the presently used hearing thresholds. In an embodiment, a hearing threshold difference measure is defined and used to determine said predefined amount. In an embodiment, the hearing threshold difference measure comprises a sum ($\Delta HT_{cur}$) of the differences between the currently estimated hearing thresholds (CEHT(f)) and the presently used hearing thresholds (PUHT(f)), where f is frequency. In an embodiment, the hearing thresholds are estimated at a number NHT of predefined frequencies, $f_1, f_2, \ldots, f_{NHT}$. In an embodiment, NHT is smaller than or equal to 12, e.g. in the range from 2 to 10. In an embodiment, the predefined frequencies comprise one or more of (such as a majority or all of) 250 Hz, 500 Hz, 1 kHz, 1.5 kHz, 2 kHz, 3 kHz, 4 kHz and 6 kHz. In an embodiment, the gain adaptation is performed with a predefined update frequency in the range from once every 6 months to once every month, or even up to once every day, or more often. In an embodiment, the update frequency is defined in relation to (e.g. determined by) the measurement time. In an embodiment, the measurement time is defined in relation to (e.g. determined by) the update frequency. In an embodiment, the gain adaptation is performed, if the relative hearing threshold difference measure ($\Delta HT_{cur}$/SUM(PUHT (f)) is larger than 10%, such as larger than 25%. In an embodiment, the gain adaptation is performed, if the rate of change (increase) of the hearing threshold difference measure (or the individual estimated hearing thresholds) is above a predefined rate, e.g. if $\Delta HT(t_2,t_1)]/(t_2-t_1)$ is larger than a predefined rate, $\Delta HT(t_2,t_1)$=SUM(EHT($f_1,t_2$)–EHT ($f_1,t_1$)), where EHT($f_1,t_n$) is the estimated hearing threshold at frequency $f_1$ (i=1, 2, ..., NHT) and time $t_n$ (n=1, 2) and where the summation (SUM) is over frequencies $f_1$. In an embodiment, the gain adaptation is performed at the request of a user via a user interface of the hearing aid (e.g. a remote control).

The ABR estimates may be used to monitor (possibly relatively short term, e.g. within hours or days) temporal threshold shifts (TTS) as a consequence of being subject to excessively loud sounds. Also here a warning to the user can be appropriate.

In an embodiment, the hearing aid is configured to issue an alarm, when a threshold value of an acoustic dose is exceeded. US 2010/141439 A1 deals with determining an accumulated sound dose and issuing an alarm to a user of a hearing aid.

In an embodiment, the hearing aid comprises an alarm indication unit adapted for issuing an alarm signal to the user in case said estimated hearing thresholds deteriorate over time.

In an embodiment, the deterioration is identified in that said estimated hearing thresholds (e.g. in dB sound pressure level (SPL)) increase above predetermined relative or absolute levels or that said rates of change of the hearing thresholds are above predefined values. Alternatively, the deterioration is identified in that said hearing threshold difference measure exceeds a predetermined threshold value.

In an embodiment, an absolute hearing threshold difference measure ($\Delta HT_{abs}$) is defined as a sum of the differences between the originally stored (or estimated) hearing thresholds (OSHT(f)) and the currently estimated hearing thresholds (CEHT(f)), where f is frequency (e.g. $\Delta HT_{abs}$=SUM (OSHT($f_1$)–CEHT($f_1$)), i=1, 2, . . . , NHT). The term 'originally stored (or estimated) hearing thresholds' is taken to mean hearing thresholds that were used when the hearing aid was initially taken into operation by the user (or at a later point in time, where the thresholds have been updated in a normal fitting procedure); such original hearing thresholds e.g. being clinically determined and stored in the hearing aid or estimated and stored by the hearing aid itself ('first time estimation'). In an embodiment, the absolute hearing threshold difference measure is used as an indicator of the (long term) hearing threshold deterioration.

In an embodiment, the hearing aid is adapted to determine at least an estimate of the real or absolute time elapsed between two time instances where estimates of hearing thresholds are determined and possibly stored. In an embodiment, the hearing aid is adapted to receive a signal representative of the present time from another device, e.g. from a cell phone or from a transmitter of a radio time signal (e.g. DCF77 or MSF). In an embodiment, the hearing aid comprises a real time clock circuit and a battery ensuring a constant functioning of the clock. In an embodiment the hearing aid comprises an uptime clock for measuring an uptime in which the hearing aid is in operation, and/or a power-up counter for counting a number of power-ups of the hearing aid, and the hearing aid is adapted to estimate a real time range elapsed from the uptime and/or the number of power-ups of the hearing aid.

In an embodiment, the alarm indication unit is adapted to issue a first alarm signal, if said deterioration rate or if said current hearing threshold difference measure is above a predefined threshold value (indicating that the user may have been exposed to an excessive acoustic dose, possibly over a relatively short period of time, and that the user should take measures to minimize such exposure).

In an embodiment, the alarm indication unit is adapted to issue a second alarm signal, if said absolute hearing threshold difference measure exceeds a predefined threshold value (indicating that the user's hearing ability has deteriorated, possibly over a relatively long period of time, and that the user should act to verify the cause of such deterioration and identify a proper remedy).

In an embodiment, the hearing aid comprises at least two separate physical bodies, each comprising a housing. In an embodiment, one part is adapted for being mounted fully or partly in an ear canal of a user (a so-called ITE-part). In an embodiment, one part is adapted for being mounted behind an ear of a user (a so-called BTE-part). In an embodiment, the ITE-part as well as the BTE-part comprises at least one electrode located at a surface of the housing of the part in question to allow the electrode or electrodes to contact the skin of a user's head when the part is operationally mounted on the user.

In an embodiment, time and frequency dependent gain of the signal processing unit is adapted to compensate for a hearing loss of a user. Various aspects of digital hearing aids are described in [Schaub; 2008].

In an embodiment, the output transducer comprises a receiver (speaker) for providing the stimulus as an acoustic signal to the user.

In an embodiment, the input transducer comprises a microphone. In an embodiment, the input transducer comprises a directional microphone system adapted to separate two or more acoustic sources in the local environment of the user wearing the hearing aid.

In an embodiment, the hearing aid comprises a (possibly standardized) electric interface (e.g. in the form of a connector to implement a wired interface or wireless interface and/or an antenna and transceiver circuitry to implement a wireless interface) for receiving a direct electric input signal from another device, e.g. a communication device or another hearing aid. In an embodiment, the direct electric input signal represents or comprises an audio signal and/or a control signal and/or an information signal. In an embodiment, the hearing aid comprises demodulation circuitry for demodulating the received direct electric input to provide the direct electric input signal representing an audio signal and/or a control signal e.g. for setting an operational parameter (e.g. volume) and/or a processing parameter of the hearing aid. In general, the wireless link established by a transmitter and antenna and transceiver circuitry of the hearing aid can be of any type. In an embodiment, the wireless link is used under power constraints, e.g. in that the hearing aid comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation. In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying) or QAM (quadrature amplitude modulation).

In an embodiment, the ear part of the hearing aid is a device whose maximum physical dimension (and thus of a possible antenna for providing a wireless interface to the device) is smaller than 10 cm, such as smaller than 5 cm, such as smaller than 2 cm.

In an embodiment, the hearing aid comprises a forward or signal path between the input transducer (microphone system and/or direct electric input (e.g. a wireless receiver)) and the output transducer. In an embodiment, the signal processing unit is located (at least partially) in the forward path. In an embodiment, the signal processing unit is adapted to provide a frequency dependent gain according to a user's particular needs. In an embodiment, the hearing aid comprises an analysis path comprising functional components for analyzing the input signal (e.g. determining a level, a modulation, a type of signal, an acoustic feedback estimate, etc.). The analysis path may further comprise functionality (e.g. implemented in the signal processing unit) that is not directly related to the current signal of the forward path, e.g. the processing of the brain signals picked up by the one or more electrodes. In an embodiment, some or all signal processing of the analysis path and/or the signal path is conducted in the frequency domain. In an embodiment, some or all signal processing of the analysis path and/or the signal path is conducted in the time domain. In an embodiment, some or all signal processing of the forward path is conducted in the time domain, whereas some or all signal processing of the analysis path in the frequency domain.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 40 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 μs, for $f_s$=20 kHz. In an embodiment, a number of audio samples are arranged in a time frame. In an embodiment, a time frame comprises 64 audio data samples. Other frame lengths may be used depending on the practical application.

In an embodiment, the hearing aids comprise an analogue-to-digital (AD) converter to digitize an analogue input with a predefined sampling rate, e.g. 20 kHz. In an embodiment, the hearing aids comprise a digital-to-analogue (DA) converter to convert a digital signal to an analogue output signal, e.g. for being presented to a user via an output transducer.

In an embodiment, the hearing aid, e.g. the input transducer, comprises a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain.

In an embodiment, the frequency range considered by the hearing aid from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing aid is split into a number NI of frequency bands, where NI is e.g. larger than 5, such as larger than 10, such as larger than 50, such as larger than 100, such as larger than 500, at least some of which are processed individually. In an embodiment, the hearing aid is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing aid comprises one or more detectors for classifying an acoustic environment around the hearing aid and/or for characterizing the signal of the forward path of the hearing aid. Examples of such detectors are a level detector, a speech detector, a feedback detector (e.g. a tone detector, an autocorrelation detector, etc.), a directionality detector, etc.

In an embodiment, the hearing aid comprises an acoustic (and/or mechanical) feedback suppression system.

In an embodiment, the hearing aid further comprises other relevant functionality for the application in question, e.g. compression, noise reduction, etc.

In an embodiment, the hearing aid comprises a hearing instrument, e.g. a hearing instrument adapted for being located at the ear or fully or partially in the ear canal of a user, e.g. a headset, an earphone, an ear protection device or a combination thereof.

Use:

In an aspect, use of a hearing aid as described above, in the 'detailed description of embodiments' and in the claims, is moreover provided. In an embodiment, use is provided in a system comprising one or more hearing instruments, headsets, ear phones, active ear protection systems, etc.

A method:

In an aspect, a method of operating a hearing aid is furthermore provided by the present application, the hearing aid comprising an ear part adapted for being mounted fully or partially at an ear or in an ear canal of a user, the ear part comprising
a housing,
at least one electrode located at a surface of said housing to allow said electrodes to contact the skin of a user when said ear part is operationally mounted on the user, and adapted to pick up a low voltage electric signal from the user's brain,
an amplifier unit operationally connected to said electrode(s) and adapted for amplifying said low voltage electric signal(s) to provide amplified brain signal(s), an input transducer for providing an electric audio input signal, an output transducer for converting an electric output signal to an acoustic output sound to a user, a signal generator for generating an electric test signal, the signal generator being operationally connected to said output transducer allowing said electric test signal to be presented to a user as an auditory test stimulus, a signal processing unit, said signal processing unit being operationally connected to said amplifier unit, to said input transducer, and to said output transducer.

The method comprises mounting said hearing aid on said user;

applying a time and frequency dependent gain to said electric audio input signal or a signal originating therefrom and providing a processed audio output signal;

generating and specifically adapting said electric test signal to be presented to the user as an auditory test stimulus and used in an auditory evoked potential, AEP, measurement;

mixing said processed audio output signal or a signal originating therefrom and said electric test signal to said electric output signal for being presented together to the user as said acoustic output sound;

recording and processing said amplified brain signal(s) to provide a processed brain signal.

It is intended that the structural features of the hearing aid described above, in the 'detailed description of embodiments' and in the claims can be combined with the method, when appropriately substituted by a corresponding process and vice versa. Embodiments of the method have the same advantages as the corresponding devices.

In an embodiment, the method comprises that the user's hearing thresholds are estimated based on the processed brain signals.

In an embodiment, the method comprises running a fitting algorithm using said estimated hearing thresholds to determine the appropriate frequency dependent gain for the user. In an embodiment, the method comprises executing the fitting algorithm in real-time.

In an embodiment, the method comprises that the (time and) frequency dependent gain is modified based on said estimated hearing thresholds.

In an embodiment, the method of measuring auditory evoked potentials is selected among Auditory Brainstem Response (ABR), including Auditory Brainstem Responses to complex sounds (cABR), Auditory Steady State Response (ASSR), and Frequency Following Response (FFR).

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing Aid System:

In a further aspect, a hearing aid system comprising a hearing aid as described above, in the 'detailed description of embodiments', and in the claims, AND an auxiliary device is moreover provided.

In an embodiment, the system is adapted to establish a communication link between the hearing aid and the auxiliary device to provide that information (e.g. control and status signals, possibly audio signals) can be exchanged or forwarded from one to the other.

In an embodiment, the auxiliary device comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing aid. In an embodiment, the auxiliary device comprises a remote control for controlling operation of the hearing aid.

In an embodiment, the auxiliary device is or comprises another hearing aid. In an embodiment, the hearing aid system comprises two hearing aids adapted to implement a binaural hearing aid system.

In an embodiment, the hearing aid system comprises another hearing aid as described above, in the 'detailed description of embodiments', and in the claims and an auxiliary device, e.g. an audio gateway and/or a remote control for the hearing aids. In an embodiment, the two hearing aids implement or form part of a binaural hearing aid system.

In an embodiment, the hearing aid system is adapted to transmit values of the amplified or processed brain signals from at least one of the hearing aids to the other. Thereby the electrodes of both hearing aids may be used together in the estimation of the hearing thresholds. In an embodiment, at least one of the electrodes is a reference electrode.

In an embodiment, the hearing aid system is adapted to transmit values of the amplified or processed brain signals from the hearing aids to the auxiliary device. The processing of the low voltage EEG-signals from the electrodes (e.g. including the estimation of hearing thresholds and resulting gains) may be fully or partially performed in the auxiliary device. This has the advantage of removing power consuming operations from the listening devices to the auxiliary device for which the size limitations and thus the power consumption constraints are less strict.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Event related potentials. ERPs can be reliably measured using electroencephalography (EEG). The (weak) potentials we are measuring are buried deep into the electrical activity of the brain. Actually the interesting signal is magnitudes below the 'brain activity noise'. This is where the benefit of systematically evoked potentials comes in. If a pre-defined sound stimulus is sent out, and if we know exactly when we have generated the sound, we can expect the weak interesting response signal after some delay. If we now send exactly the same signal again, the weak response will be the same again but the ambient noise was different. If we then add (or average) the two responses and assume that the weak response is independent of the ambient/brain activity noise then the weak response will be added in magnitude and phase while the two independent noise samples most probably will cancel parts of the noise since the two noise samples are unrelated when you add/average. If this procedure is repeated hundreds or thousands or more times the estimate of the weak response will be more and more certain since several thousand or more responses are added in magnitude and phase, while the uncorrelated noise parts will cancel each other in the adding/averaging process since they are uncorrelated samples. The very nice property with the electrode equipped hearing aid doing this procedure is that this procedure/averaging can be sustained for very long time (days, weeks, months) and thereby a much more certain estimate of the response can be obtained compared to a time limited clinical measure (in the clinic you will need a silent room resting on a couch to be able to get a stable ERP in a few minutes due to limited clinical time).

Figure 1A:
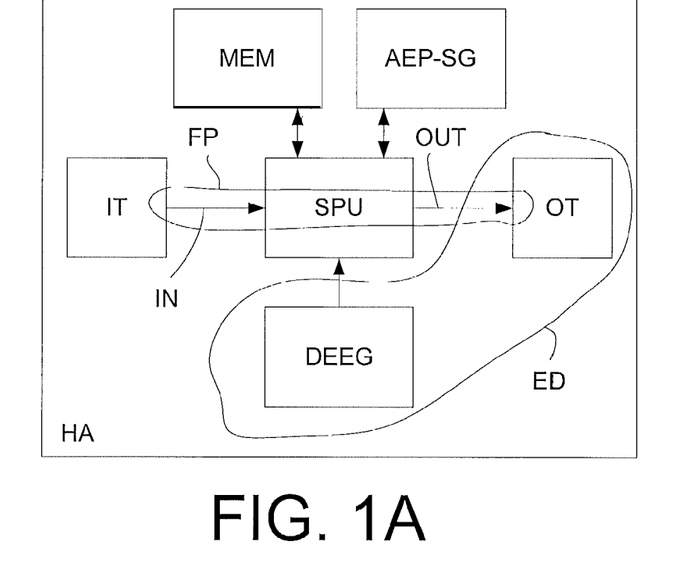
FIGS. 1A and 1B show a first embodiment of a hearing aid according to the present disclosure.
Figure 1B:
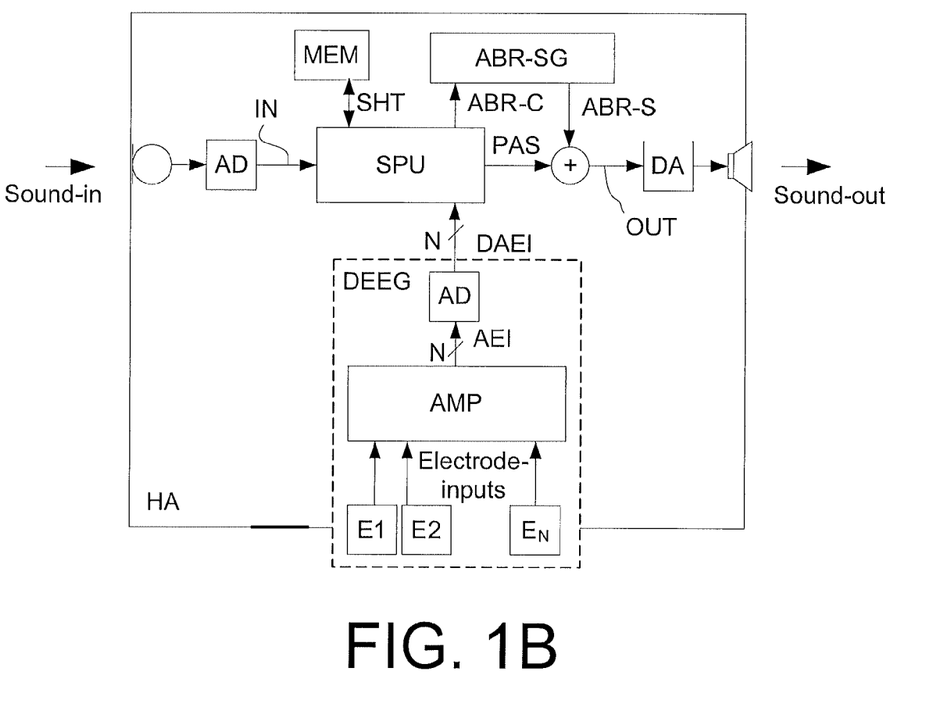

FIG. 1 shows a first embodiment of a hearing aid according to the present disclosure. FIG. 1A shows a hearing aid (HA) comprising a forward or signal path (FP) from an input transducer (IT) to an output transducer (OT) the forward path being defined there between and comprising a signal processing unit (SPU) for (among other things) applying a frequency dependent gain to the audio signal picked up by the input transducer (IT, e.g. as in FIG. 1B a microphone unit) and providing an enhanced signal to the output transducer (OT, e.g. as in FIG. 1B a loudspeaker). The hearing aid comprises an EEG unit (DEEG) for picking up and amplifying low voltage electric signals from the user's brain and providing corresponding (here digital) amplified brain signals ($DAEI_1$-$DAEI_N$, where N is the number of electrodes picking up the low voltage electric signal, cf. FIG. 1B). The signal processing unit is adapted to determine a user's hearing thresholds based on the amplified brain signal(s) from the EEG unit (DEEG). The hearing aid further comprises a memory (MEM) for storing the sets of hearing thresholds as determined in the signal processing unit at different points in time ($t_1, t_2, \ldots, t_n$). The hearing aid further comprises a stimulus signal generator (AEP-SG) for generating an electric test signal specifically adapted to be used in an auditory evoked potential (AEP, e.g. a brain stem response (ABR)) measurement. The stimulus signal generator is operationally connected to the output transducer (OT) via the signal processing unit (SPU) allowing the electric test signal to be mixed with the processed audio signal and converted to an auditory test stimulus for being presented to a user together with the acoustic version of the processed audio signal. Preferably, the electric test signal is inaudible to the user (e.g. masked). The signal processing unit is adapted to control the stimulus signal generator (AEP-SG), e.g. to provide that the electric stimulus signal is masked when combined with the processed audio signal. In an embodiment, the EEG unit (DEEG) comprising the electrodes is enclosed in an ear part comprising a housing adapted for being mounted fully or partially at an ear or in an ear canal of a user. The electrodes are located at a surface of the housing to allow the electrodes to contact the skin of the user when the ear part is operationally mounted at or in an ear of the user. In an embodiment, the ear part (ED) further comprises the output transducer (OT) as indicated by the curved enclosure in the embodiment of FIG. 1A. In an embodiment, all the mentioned components of the hearing aid (HA) and enclosed in the solid rectangle are enclosed in the same common housing adapted for being mounted fully or partially at an ear or in an ear canal of a user. Other partitions of the components in two or more separate bodies may be implemented depending on the application in question.

In the more detailed embodiment of the hearing aid of FIG. 1A shown in FIG. 1B, the main part of the signal processing of the hearing aid (HA) is digital, so the forward path further comprises an analogue-to-digital (AD) converter to digitize an analogue audio input from the microphone with a predefined sampling rate, e.g. 20 kHz, and a digital-to-analogue (DA) converter to convert a digital signal from the signal processing unit (SPU) to an analogue output signal, which is fed to the loudspeaker. The forward path of the hearing aid thus converts an input sound (Sound-in) to an analogue electric input signal (by a microphone unit), which is digitized (unit AD), providing digitized input signal IN, and processed (unit SPU), and the processed output signal OUT is converted to an analogue signal (unit DA), which is converted (by a speaker unit) to an output sound (Sound-out). The EEG unit (cf. dashed rectangular outline DEEG) comprises N electrodes $E_1, E_2, \ldots, E_N$, each being adapted to pick up a low voltage electric signal from the user's brain when located in contact with the user's skin at different locations of the head of the user (e.g. at or in an ear). The EEG unit further comprises an amplifier unit (AMP) operationally connected to the N electrodes and adapted for amplifying the low voltage electric signals (Electrode inputs) from the electrodes and to provide amplified brain signals $AEI_1, AEI_2, \ldots, AEI_N$. The EEG unit further comprises an analogue-to-digital (AD) converter to digitize the analogue inputs from the amplifier and to provide digital amplified brain signals $DAEI_1, DAEI_2, \ldots, DAEI_N$, which are fed to the signal processing unit (SPU) for further processing. The digital amplified brain signals are used in the signal processing unit (SPU) to determine a user's hearing thresholds (at different frequencies and) at different points in time ($t_1, t_2, \ldots, t_n$). These are stored in memory (MEM), cf. e.g. FIG. 6. The memory (MEM) is operationally connected to the signal processing unit (SPU), via signal SHT, to allow storage and retrieval of data in/from the memory, including the mentioned sets of hearing thresholds, controlled by the signal processing unit. In the embodiment of FIG. 1B, the stimulus signal ABR-S from signal generator (ABR-SG) is fed to the sum unit '+' together with the processed audio signal PAS. The resulting output signal OUT is fed to the output transducer (here a speaker) allowing the electric test signal to be converted to an auditory test stimulus for being presented to a user together with the processed acoustic signal. The signal processing unit (SPU) is adapted to control the stimulus signal generator (ABR-SG) via control signal ABR-C.

Figure 2:
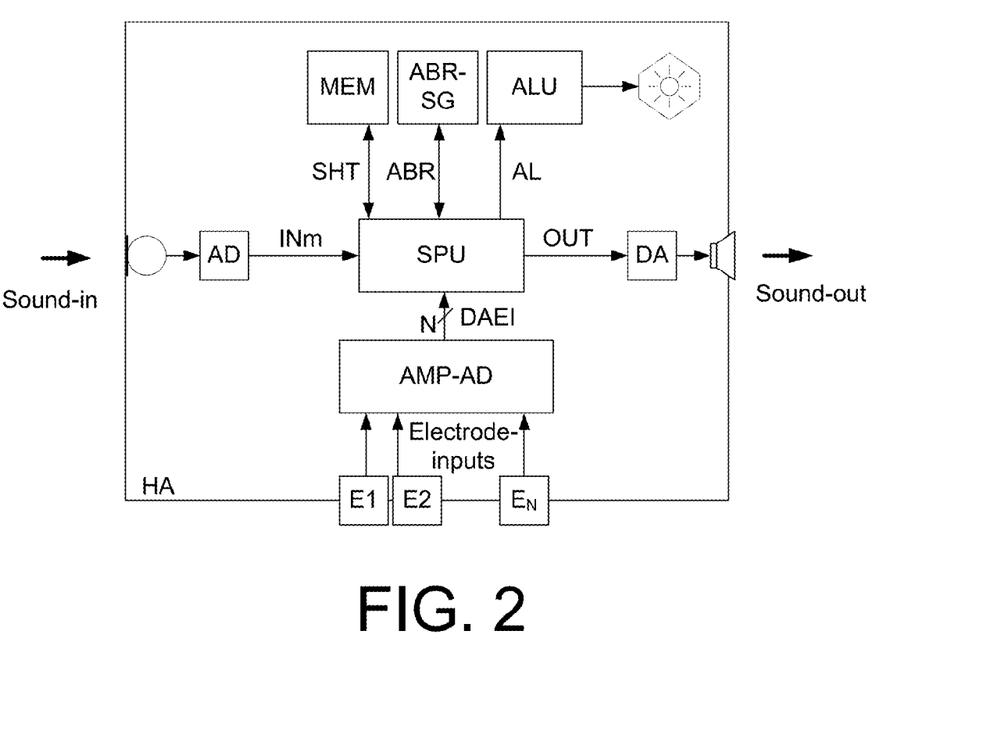
FIG. 2 shows a second embodiment of a hearing aid according to the present disclosure.

FIG. 2 shows a second embodiment of a hearing aid according to the present disclosure. The hearing aid HA of FIG. 2 comprises the same functional units as the hearing aid discussed in connection with FIG. 1B. However, the embodiment of a hearing aid of FIG. 2 further comprises an alarm indication unit (ALU) adapted for issuing a warning or information signal to a user of the hearing aid (or to another person in the user's environment). The signal processing unit (SPU) is adapted to determine a hearing threshold difference measure comprising a sum ($\Delta HT_{cur}$) of the differences between currently estimated hearing thresholds (CEHT(f)) and presently used hearing thresholds (PUHT (f)), where f is frequency. In an embodiment, the hearing thresholds are estimated at a number NHT of predefined frequencies, $f_1, f_2, \ldots, f_{NHT}$. The signal processing unit (SPU) is e.g. adapted to determine when the hearing threshold difference measure exceeds a predetermined threshold value and (in such case) to generate an alarm signal AL which is fed to the alarm indication unit (ALU). The alarm indication unit is adapted to issue a corresponding alarm (e.g. a visual and/or mechanical and/or acoustic alarm) in response to the alarm signal AL. Alternatively or additionally, the alarm signal may be transmitted to another device (e.g. via a network), e.g. for presentation to a caring person or an audiologist. Another difference is that the stimulus signal generator (ABR-SG) for generating an electric test signal for use to initiate an auditory brain stem response (ABR) is combined with the processed audio signal in the signal processing unit (instead of via SUM-unit ('+') in FIG. 1B. The combined signal OUT is fed to the DA converter connected to the loudspeaker. Further, the analogue to digital conversion unit (AD) of the embodiment of FIG. 1B is integrated with the amplifier unit (AMP) in FIG. 2 (cf. unit AMP-AD in FIG. 2).

Figure 3:
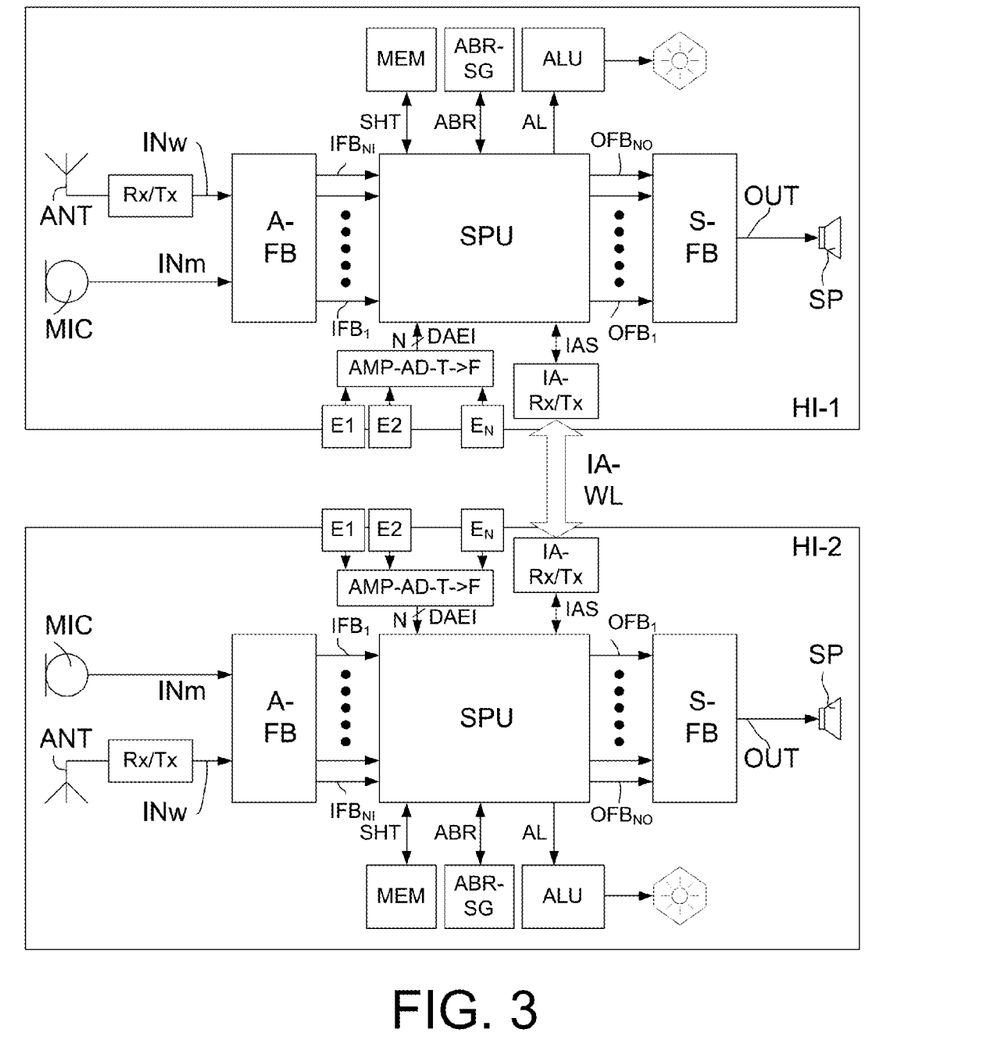
FIG. 3 shows an embodiment of a binaural hearing aid system comprising first and second hearing instruments according to the present disclosure.

FIG. 3 shows an embodiment of a binaural hearing aid system comprising first and second hearing instruments according to the present disclosure. The binaural hearing aid system comprises first and second (possibly, as in FIG. 3, essentially identical) hearing instruments (HI-1, HI-2) adapted for being located at or in left and right ears of a user. The hearing instruments (HI-1, HI-2) of FIG. 3 are similar to the embodiment of a hearing aid (HA) shown in FIG. 2. The hearing instruments (HI-1, HI-2) are additionally adapted for exchanging information between them via a wireless communication link, e.g. a specific inter-aural (IA) wireless link (IA-WL). The two hearing instruments HI-1, HI-2 are adapted to (at least) allow the exchange of status signals, e.g. including the transmission of characteristics of the input signal received by a device at a particular ear to the device at the other ear, and/or (amplified) EEG-data (e.g. signals DAEI(1:N) or signals derived therefrom) picked up by one or more electrodes ($E_1, E_2, \ldots, E_N$) of the contra-lateral hearing instrument, cf. signal IAS. To establish the inter-aural link, each hearing instrument comprises antenna and transceiver circuitry (here indicated by block IA-Rx/Tx). Each of the hearing instruments of the binaural hearing aid system of FIG. 3 comprises two different input transducers, 1) a microphone unit (MIC) for converting an acoustic input sound to a first electric audio signal INm, and 2) a wireless transceiver (at least a receiver) (ANT and Rx/Tx-unit) for receiving (and possibly transmitting) a signal from another device, e.g. an audio signal INw. The hearing instruments HI-1, HI-2 are (in this embodiment) assumed to process the audio signal of the forward path in the frequency domain, and therefore each comprise analysis (A-FB) and synthesis (S-FB) filter banks after and before the input (MIC and ANT, Rx/Tx) and output (SP) transducers, respectively. The analysis filter bank (A-FB) is adapted for splitting the (time varying) input signals (INm, INw) into a number NI of (time varying) signals $IFB_1, IFB_2, \ldots, IFB_{NI}$, each comprising a distinct frequency range of the input signal. The input transducer (MIC and ANT, Rx/Tx) or the analysis filter bank (A-FB) is assumed to comprise an analogue to digital converter (AD). Correspondingly, the synthesis filter bank (S-FB) is adapted for merging the a number NO of (time varying) signals $OFB_1, OFB_2, \ldots, OFB_{NO}$, each comprising a distinct frequency range of the output signal into a (time varying) output signal (OUT), which is fed to the output transducer (SP) for conversion to an output sound for presentation to the user. The output transducer (SP) or the synthesis filter bank (S-FB) may comprise a digital to analogue converter (DA). Each of the hearing instruments HI-1, HI-2 comprises the same functional units as discussed for the hearing aid of FIG. 2, including the EEG-data generating units (electrodes $E_n$ and amplifier and analog to digital converting unit AMP-AD). In the embodiments of hearing instruments HI-1, HI-2 of FIG. 3, the amplifier blocks further comprise a time to time-frequency conversion functionality (as indicated by the name of the amplifier unit AMP-AD-T→F) to provide the digital amplified brain signals ($DAI_1, DAI_2, \ldots, DAI_N$) in the frequency domain to adapt to further signal processing of the brain signals (determining the frequency dependent hearing thresholds) which may be performed by the signal processing unit (SPU) in the frequency domain. The same may be the case for the signal IAS from the opposite hearing instrument, in which case a T→F conversion unit is included in the IA-Rx/Tx transceiver unit. The number of frequency units provided by the time to time-frequency conversion functionality may or may not be equal to the number NI of frequency bands of the forward path (e.g. smaller than NI). Alternatively the digital amplified brain signals may be further processed in the signal processing unit (SPU) in the time domain, in which case the time to time-frequency conversion functionality of the amplifier can be omitted.

Figure 5:
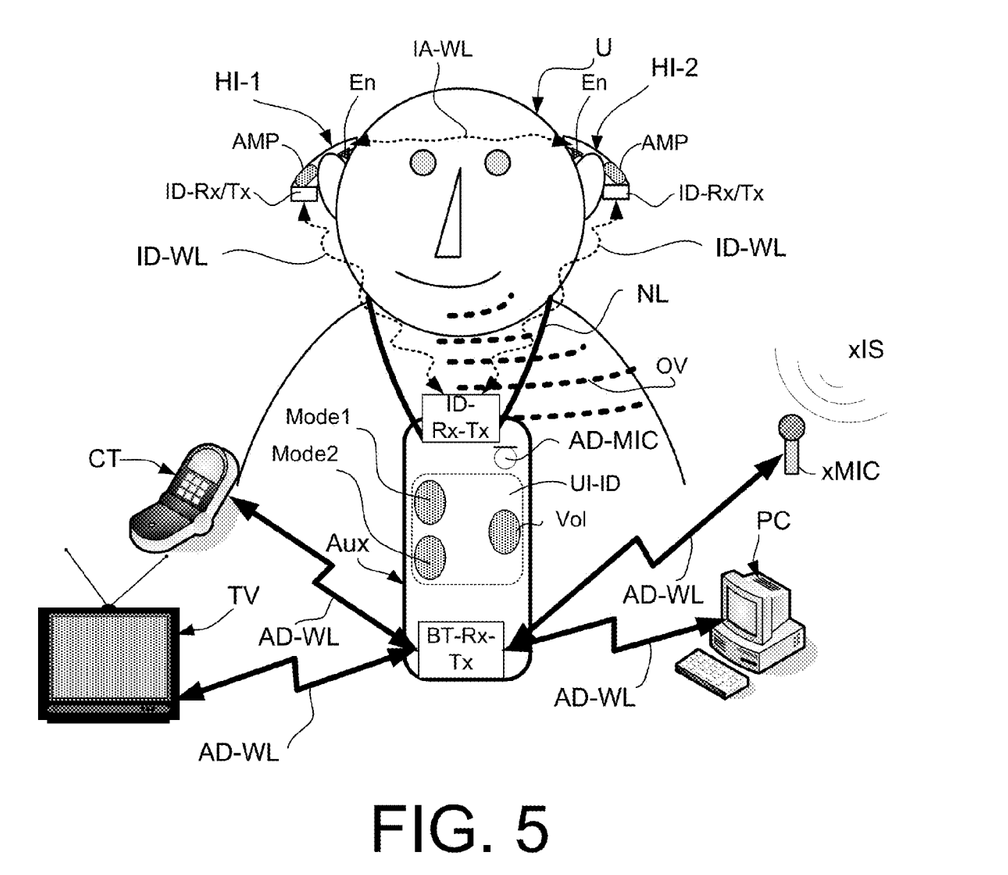
FIG. 5 shows an application scenario comprising an embodiment of a binaural hearing aid system comprising first and second hearing instruments and an auxiliary device according to the present disclosure.

In an embodiment, the hearing aid system further comprises an auxiliary device, e.g. an audio gateway device for receiving a number of audio signals and for transmitting at least one of the received audio signals to the hearing instruments (cf. transceivers (ANT, Rx/Tx in FIG. 3), as e.g. illustrated in FIG. 5. In an embodiment, the listening system is adapted to provide that a telephone input signal can be received in the hearing instrument(s) via the audio gateway. In an embodiment, the hearing aid system comprises a remote control acting as a user interface to the hearing instruments, e.g. to allow a user to change program (e.g. to activate or deactivate the ABR-recordal) or otherwise modify operational parameters of the hearing instruments, e.g. output volume of the loudspeaker. In an embodiment, the remote control and the audio gateway are integrated into the same communications device (as e.g. illustrated in FIG. 5). The processing of (amplified) EEG-data (e.g. signals DAEI(1:N) of the hearing instruments, or signals derived therefrom) picked up by the one or more electrodes ($E_1, E_2, \ldots, E_N$) may be fully or partially performed in the auxiliary device (e.g. in the audio gateway/remote control device).

Figures 4A, 4B, 4C, 4D:
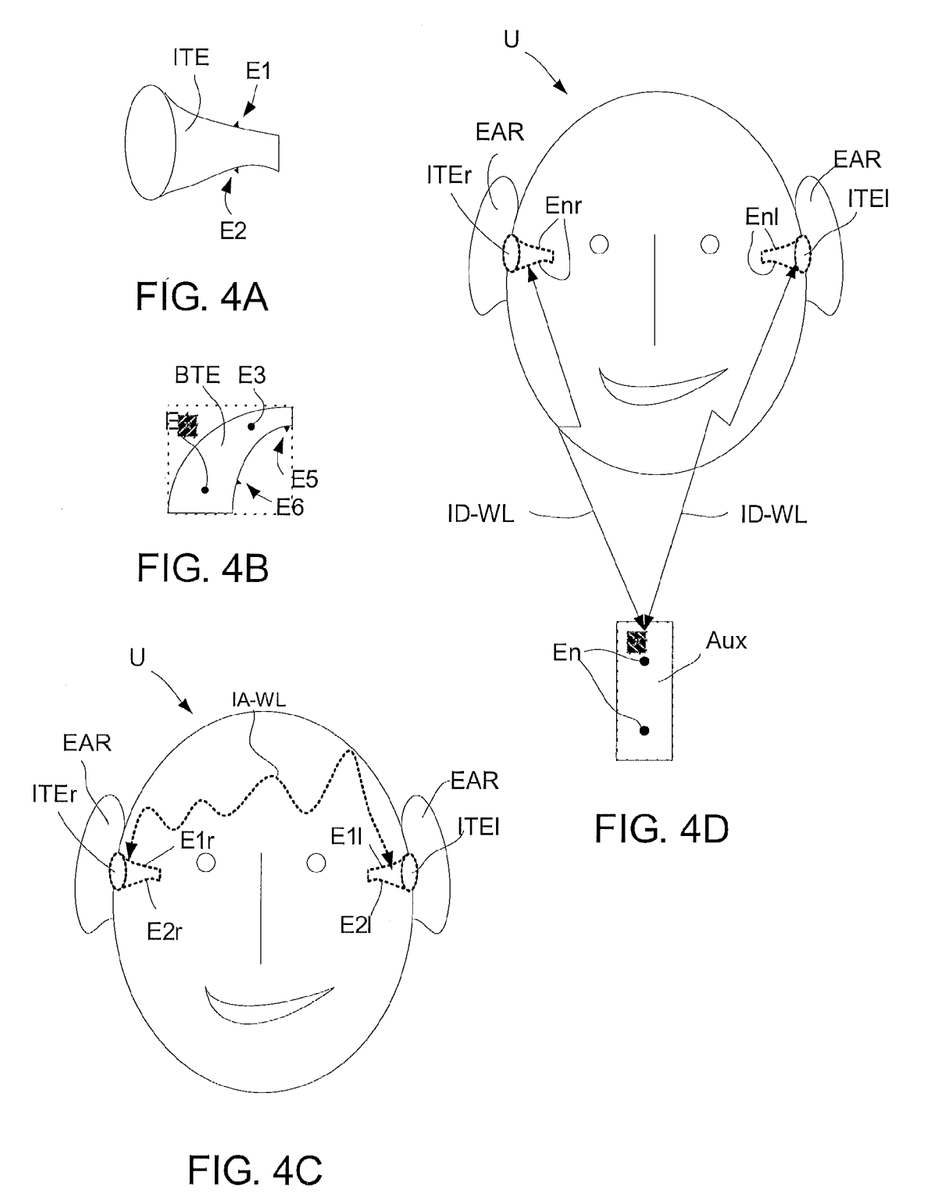
FIGS. 4A, 4B, 4C and 4D show various elements of embodiments of a binaural hearing aid system according to the present disclosure.

FIG. 4 shows various elements of embodiments of a binaural hearing aid system according to the present disclosure. FIG. 4A shows an 'in the ear' part (ITE) of a hearing aid. In an embodiment, the ITE part constitutes the hearing aid. The ITE part is e.g. adapted for being located fully or partially in the ear canal of the user U (cf. FIG. 4C, 4D). The ITE part comprises two electrodes E1, E2 located on (or extending from) the surface of the housing of the ITE part. The ITE part e.g. comprises a mould adapted to a particular user's ear canal. The mould is typically made of a form stable plastic material by an injection moulding process or formed by a rapid prototyping process, e.g. a numerically controlled laser cutting process (see e.g. EP 1 295 509 and references therein). A major issue of an ITE part is that it makes a tight fit to the ear canal. Thus, electrical contacts on the surface (or extending from the surface) of the mould contacting the walls of the ear canal are inherently well suited for forming an electrical contact to the body. FIG. 4B shows another embodiment of a (part of a) hearing aid according to the disclosure. FIG. 4B shows a part (BTE) of a 'behind the ear' hearing aid, where the BTE part is adapted for being located behind the ear (pinna, EAR in FIGS. 4C and 4D) of a user U. The BTE part comprises four electric terminals E3, E4, E5, E6, two of which are located on the face of the BTE part, which is adapted for being supported by the ridge where the ear (Pinna) is attached to the skull and two of which are located on the face of the BTE part adapted for being supported by the skull. The electric terminals (electrodes) are specifically adapted for picking up electric (e.g. brain wave) signals from the user's body, in particular from the brain, or related to a measure of cognitive load of the user. The electrical terminals may all serve the same purpose (e.g. measuring EEG) or different purposes. Electrical terminals (electrodes) for forming good electrical contact to the human body are e.g. described in literature concerning EEG-measurements (cf. e.g. US 2002/028991 or U.S. Pat. No. 6,574,513).

FIG. 4C shows an embodiment of a binaural hearing aid system according to the present disclosure comprising first and second hearing aids comprising (or being constituted by) left and right ear parts ITEl and ITEr, respectively, adapted for being located in left and right ear canals of a user, respectively (each ITE ear part being an ear part as shown in FIG. 4A). Alternatively or additionally, the left and right hearing aids may comprise left and right ear parts BTEl and BTEr, respectively, adapted for being located behind left and right ears of a user, respectively (each BTE ear part being an ear part as shown in FIG. 4B). The electric terminals (E1l, E2l and E1r, E2r of the left and right parts, respectively) are adapted to pick up a relatively low voltage (from the body) and is operationally connected to an amplifier for amplifying the low voltage signals and to transmit a value representative of the amplified voltage to a signal processor of the hearing aid (e.g. located in the ITE-part, in a BTE-part or in an auxiliary device, e.g. unit Aux in FIG. 4D or audio gateway/remote control (Aux) in FIG. 5). Preferably, the hearing aid system comprises a reference terminal. At least one of the left and right hearing aids or hearing aid parts is adapted to allow transmission of signals from the (amplified, EEG) voltages picked up by the electrodes of the hearing aid in question to the other hearing aid (or to an auxiliary device performing the further processing of the voltages from (all) the electrodes) to allow the estimate of hearing thresholds of the user to be based on all available electrodes. Preferably, each of the hearing aids (ITEl, ITEr) comprises antenna and transceiver circuitry to establish an interaural wireless link (IA-WL) between the two hearing aids as illustrated in FIG. 3.

FIG. 4D shows an embodiment of a binaural hearing aid system according to the present disclosure, which additionally comprises a number of electric terminals or sensors contributing to an estimate of the present cognitive load and/or a classification of the present environment of the user. The embodiment of FIG. 4D is identical to that of FIG. 4C apart from additionally comprising a body-mounted auxiliary device (Aux) optionally having 2 extra electric terminals, e.g. EEG electrodes, (En) mounted in good electrical contact with body tissue (but NOT on the head). In an embodiment, the auxiliary device (Aux) comprises amplification and processing circuitry to allow a processing of the signals picked up by the electric terminals En. In that case the auxiliary device (Aux) can act as a sensor and provide a processed input to the estimate of present cognitive load of the user (e.g. the estimate itself). The auxiliary device and at least one of the hearing aids (ITEl, ITEr) each comprise a wireless interface (comprising corresponding transceivers and antennas) for establishing a wireless link (ID-WL) between the devices for use in the exchange of data between the body-mounted auxiliary device (Aux) and the hearing aid(s) (ITEl, ITEr). In an embodiment, the hearing aids (ITEl, ITEr) transmit the amplified voltages picked up by their respective electrodes to the auxiliary device, where the estimate of the hearing thresholds of the (left and/or right ears of the) user is performed. This has the advantage that the (power consuming) ABR-processing can be performed in the (larger) auxiliary device, which typically can be equipped with an energy source of larger capacity than that of a hearing aid (due to the different size constraints). In this case, the interaural link (IA-WL) of the embodiment of FIG. 4C may be dispensed with for the sake of the calculation of hearing thresholds (and corresponding required frequency dependent gains). In such case, the wireless links ID-WL between the auxiliary device and each of the hearing aids is preferably bidirectional, allowing the auxiliary device to forward revised hearing thresholds or gains to the hearing aids, when the hearing thresholds determined in the auxiliary device have changed more than predefined amounts. The wireless link may be based on near-field (capacitive or inductive coupling) or far-field (radiated fields) electromagnetic fields. The voltages from the electrodes of the auxiliary device may e.g. be used to classify ('lifter') the voltages from the head mounted electrodes of the hearing aids, e.g. based on the correlation between the signals picked up by the head worn and body worn electrodes, respectively. This may e.g. be used to filter out time segments of the recorded brain wave signals comprising distortions, e.g. 'incidents' of non-reflexive (e.g. willful) influence of the user on the brainwave signals. In an embodiment, the voltages picked up by the head worn electrodes (which are used for the estimate of hearing thresholds of the user) are NOT particularly related to hearing, if the correlation with the voltages picked up by the body worn electrodes is large (e.g. above a predefined value, depending on the specific correlation measure used).

FIG. 5 shows an application scenario comprising an embodiment of a binaural hearing aid system comprising first and second hearing instruments (HI-1, HI-2) and an auxiliary device (Aux) according to the present disclosure. The auxiliary device (Aux) comprises an audio selection device adapted for receiving a multitude of audio signals (here shown from an entertainment device, e.g. a TV (TV), a telephone apparatus, e.g. a cellular telephone (CT), a computer, e.g. a PC (PC), and an external microphone (xMIC) for picking up sounds xIS from the environment, e.g. the voice of another person). In the embodiment of FIG. 5, the microphone (AD-MIC) of the audio gateway device is adapted for picking up the user's own voice (OV) and to be capable of being connected to one or more of the external audio sources via wireless links (AD-WL), here assumed to be in the form of digital transmission links according to the Bluetooth standard as indicated by the Bluetooth transceiver (BT-Rx-Tx) in the audio gateway device (Aux). The links may alternatively be implemented in any other convenient wireless and/or wired manner, and according to any appropriate modulation type or transmission standard, possibly different for different audio sources. Other audio sources than the ones shown in FIG. 5 may be connectable to the audio gateway, e.g. an audio delivery device (such as a music player or the like). The audio gateway device of FIG. 5 further has the function of a remote control of the hearing aids, e.g. for changing program or operating parameters (e.g. volume, cf. Vol-button) in the hearing aids, cf. user interface UI-ID. In the context of the present disclosure, the remote control functions of the auxiliary device (Aux) further comprises activation or deactivation of the ABR part of the hearing aid (including disabling the generation of (acoustic) ABR-stimuli and the processing of the voltages picked up by the electrodes of the hearing aids). This can e.g. be defined by one or more special modes that are selectable via mode buttons (Mode1, Mode2) of the user interface (UI-ID) on the auxiliary device (or via a touch sensitive display or any other appropriate activation element). Other 'normal' modes of operation of the binaural hearing aid system may likewise be selected by the user via the user interface (UI-ID).

The hearing instruments (HI-1, HI-2) are shown as devices mounted at the ear (behind the ear) of a user U. Each of the hearing instruments comprise a wireless transceiver, here indicated to be based on inductive communication (ID-Rx/Tx). The transceiver (at least) comprises an inductive receiver (i.e. comprising an inductive coil, which is inductively coupled to a corresponding coil in a transceiver (ID-Rx-Tx) of the audio gateway device (Aux)), which is adapted to receive an audio signal from the audio gateway device and any additional control or information signals. The inductive link ID-WL between the audio gateway device and the hearing instruments is indicated to be two-way, but may alternatively be one-way (from the auxiliary device to each of the hearing instruments).

The audio gateway device Aux is shown to be carried around the neck of the user U in a neck-strap (NL). The neck-strap NL may have the combined function of a carrying strap and a loop antenna into which the audio signal from the audio gateway device is fed for better inductive coupling to the inductive transceiver of the listening device. An audio selection device, which may be modified and used according to the present invention is e.g. described in EP 1 460 769 A1, EP 1 981 253 A1 and in WO 2009/135872 A1.

Figure 6:
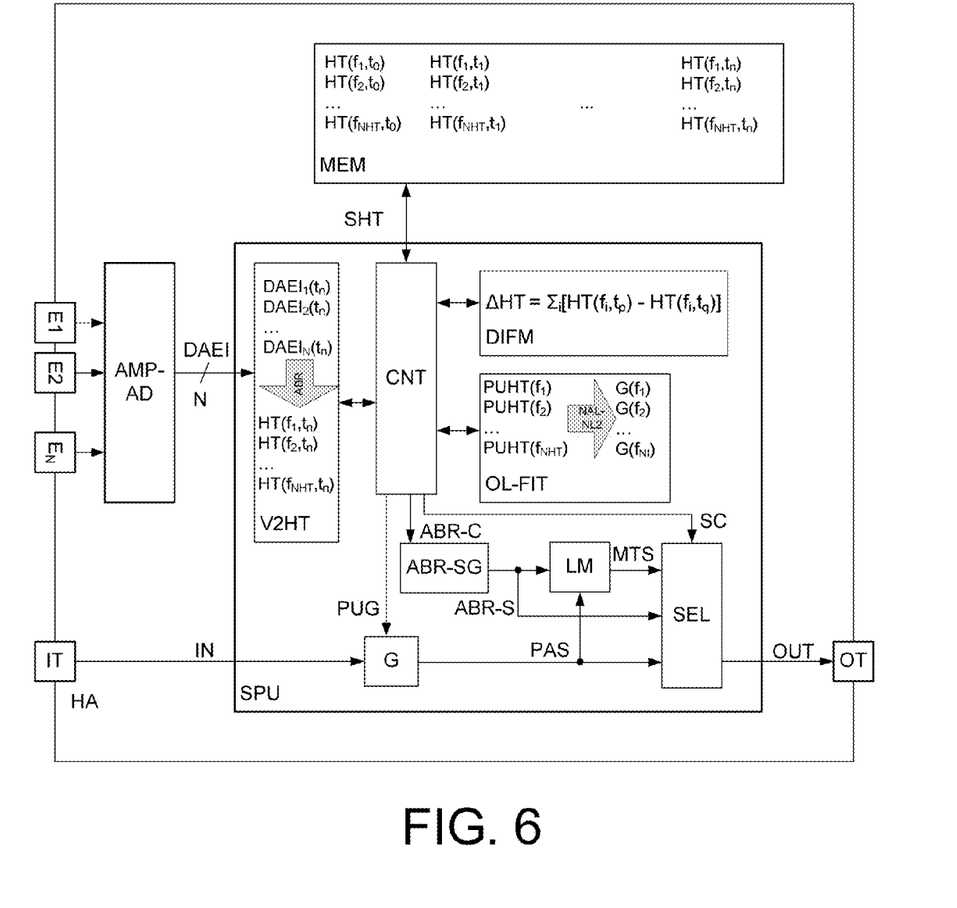
FIG. 6 shows a third embodiment of a hearing aid according to the present disclosure.

FIG. 6 shows a third embodiment of a hearing aid according to the present disclosure. The hearing aid of FIG. 6 comprises the same functional elements as the embodiment of FIG. 1B. The memory MEM is shown to have different sets of estimated hearing thresholds HT(f,t) of the user of the hearing aid as determined from the on-board auditory evoked potential (e.g. an auditory brainstem response) system. The on-board auditory brainstem response system comprises test-signal generator (ABR-SG) and loudness model (LM) for providing masked electric stimuli (for being converted to acoustic stimuli via output transducer (OT)) and EEG-unit comprising electrodes ($E_1$-$E_N$) and corresponding amplifier and AD-converter (AMP-AD) for providing digital amplified brain signals ($DAEI_1$-$DAEI_N$). The signal processing unit (SPU) calculates (cf. sub-unit V2HT) a set of estimates of the users hearing threshold $HT(f_i,t_n)$ at frequencies $f_i$ ($i=1, 2, \ldots, NHT$) at time instance n ($t_n$) based on the digital amplified brain signals ($DAEI_1$-$DAEI_N$) at time $t_n$, such signals being preferably averaged over a measurement time, e.g. over a number of hours or days). These are stored in the memory (MEM), cf. signal SHT. The signal processing unit is adapted to store such sets of estimates of the users hearing threshold $HT(f_i,t_n)$ in the memory according to a predefined scheme, e.g. with a predefined frequency. Each set of hearing threshold estimates may correspond to a particular measurement time (or accumulated measurement time). The memory (MEM) is shown to include n+1 sets of hearing thresholds corresponding to times $t_0$, $t_1$, $t_2$, . . . , $t_n$. The first set of hearing thresholds corresponding to time $t_0$ may e.g. be a set of hearing thresholds that are stored during a fitting procedure, e.g. based on clinical measurements. Otherwise, they may represent the first set of hearing thresholds determined by the hearing aid system (e.g. in case NO fitting has been performed). The hearing thresholds are used to calculate an appropriate gain to be used in the gain unit (G) and (possibly in amended form depending on the input signal in question) applied to the input audio signal IN from the input transducer (IT) (or a signal derived therefrom, e.g. a feedback corrected input signal) to provide a processed audio signal PAS, which is fed to selector unit SEL. The frequency dependent gains ($G(f_i)$, $i=1, 2, \ldots, NI$) to be used in the gain unit (G) of the forward path are determined in the sub-unit OL-FIT from hearing thresholds $PUHT(f_i)$ defined by the control unit (CNT) to be presently used at a given time. This involves the use of a fitting algorithm, such as e.g. NAL-NL2. The 'presently used hearing thresholds' (PUNT) may e.g. be equal to a particular one of the sets of stored hearing thresholds $HT(f_i, t_n)$, e.g. the one last determined by the sub-unit V2HT, or to an average of a number of the stored sets of hearing thresholds, etc. The presently used gains $G(f_i)$ determined by the sub-unit OL-FIT are forwarded to the gain unit G via signal PUG. A test signal for the ABR-system is generated in the ABR-SG unit, e.g. as a sum of a series of three or more pure tones, each having a specified frequency, amplitude and phase, and wherein a frequency difference between the successive pure tones in the series is constant, $f_s$, cf. e.g. WO 2006/003172 A1. The test signal ABR-S is fed to a psycho acoustic model (here a loudness model), cf. unit LM, together with the processed audio signal PAS, to generate a masked test signal MTS, which is preferably inaudible to the user when combined with the processed audio signal PAS. The masked test signal MTS forming the output of the LM unit and comprising the processed audio signal in combination with the test stimuli is fed to the selector unit SEL. The pure test signal ABR-S is also fed to the selector unit SEL. The resulting output OUT from the selector unit (SEL) (for presentation to a user via output transducer OT) can be either of a) the masked test signal MTS, b) the pure test signal ABR-S or c) the processed audio signal PAS. The output signal from the selector unit is controlled by control signal SC from control unit (CNT). The signal processing unit further comprises sub-unit DIFM for calculating a hearing threshold difference measure $\Delta HT = SUM[HT(f_i, t_p) - HT(f_i, t_q)]$, $i=1, 2, \ldots$, NHT, where NHT is the number of frequencies where the hearing threshold estimates are determined, and $t_p$ and $t_q$ are different points in time, for which a set of hearing threshold estimates has been stored. From the stored sets of hearing threshold estimates and the corresponding times, various difference measures can be determined, including indications of rates of change of the hearing thresholds. Preferably, the hearing aid (HA) comprises an alarm indication unit (cf. e.g. FIG. 2, 3) adapted for issuing an alarm or warning, when a difference measure (as determined in sub-unit DIFM) is above a predefined value. Such alarm indication unit can e.g. be implemented, if operationally coupled to the control unit (CNT).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

REFERENCES

[Stürzebecher et al., 2006] Stürzebecher, E., Cebulla, M., Elberling. C., and Berger, T., *New efficient stimuli for evoking frequency-specific auditory steady-state responses*, J. Am. Acad. Audiol. 17, 448-461, 2006.

[Lunner, 2010] Lunner T., A method of operating a hearing instrument based on an estimation of present cognitive load of a user and a hearing aid system, European patent application, EP 2 200 347 A2 (23 Jun. 2010).

[Kidmose and Westermann, 2010] Kidmose P. and Westermann S. E., EEG monitoring device and method for presenting messages therein, International patent application, WO 2010/149157 A1 (29 Dec. 2010).

[Kidmose and Mandic, 2011] Kidmose P. and Mandic D. P., A hearing aid adapted for detecting brain waves and a method for adapting such a hearing aid, International patent application, WO 2011/006681 A1 (20 Jan. 2011).

WO 2006/003172 A1 (MAICO) 12 Jan. 2006.

[Fastl & Zwicker, 2007] H. Fastl, E. Zwicker, Psychoacoustics, Facts and Models, $3^{rd}$ edition, Springer, 2007, ISBN 10 3-540-23159-5

[Schaub; 2008] Arthur Schaub, Digital hearing Aids, Thieme Medical. Pub., 2008.

[Sörqvist et al.; 2012?] Patrik Sörqvist, Stefan Stenfelt, and Jerker Rönnberg, *Working Memory Capacity and Visual-Verbal Cognitive Load Modulate Auditory-Sensory Gating in the Brainstem: Towards a Unified View of Attention*, Accepted for publication in Journal of Cognitive Neuroscience

[Wiki-AEP] http.://en.wikipedia.org/wiki/Auditory_evoked_potential.

[Wiki-ABR] http://en.wikipedia.org/wiki/Auditory_brainstem_response.

[Skoe & Kraus, 2010] Erika Skoe and Nina Kraus, *Auditory Brain Stem Response to Complex Sounds: A Tutorial*, Ear and Hearing, Vol. 31, No. 3, 2010, pp. 302-324.

[Wiki-ERP] http://en.wikipedia.org/wiki/Event-related_potential

U.S. Pat. No. 7,035,745 (Stürzebecher) 27 Jan. 2005
US 2002/028991 (MEDTRONIC) 7 Mar. 2002
U.S. Pat. No. 6,574,513 (BRAINMASTER) 3 Jun. 2003
EP 1 460 769 A1 (PHONAK) 22 Sep. 2004
EP 1 981 253 A1 (OTICON) 15 Oct. 2008
WO 2009/135872 A1 (OTICON) 12 Nov. 2009
EP 1 295 509 (PHONAK) 26 Mar. 2003

The invention claimed is:

1. A hearing aid, comprising:
    an ear part configured to be mounted fully or partially at an ear or in an ear canal of a user, the ear part including
        a housing, and
        at least one electrode located at a surface of said housing to allow said at least one electrode to contact the skin of a user when said ear part is operationally mounted on the user, the at least one electrode configured to pick up at least one low voltage electric signal from the user's brain;
    an amplifier unit operationally connected to said at least one electrode and configured to amplify said at least one low voltage electric signal to provide at least one amplified brain signal;
    an input transducer for providing an electric audio input signal;
    an output transducer for converting an electric output signal to an acoustic output sound;
    a signal processing unit being operationally connected
        to said amplifier unit and configured to process said at least one amplified brain signal to provide at least one processed brain signal,
        to said input transducer and configured to apply a time and frequency dependent gain to said electric audio input signal or a signal originating therefrom and to provide a processed audio output signal, and
        to said output transducer allowing said processed audio output signal to be presented to the user as a processed acoustic signal; and
    a signal generator for generating an electric test signal specifically configured to be used in an auditory evoked potential measurement, the signal generator being operationally connected to said output transducer allowing said electric test signal to be converted to an auditory test stimulus for being presented to the user together with said processed acoustic signal during normal daily life use of the hearing aid.

2. A hearing aid according to claim 1 wherein said electric test signal is configured to provide that the auditory test stimulus is masked and/or inaudible to the user.

3. A hearing aid according to claim 1 wherein said signal processing unit is configured to estimate the user's hearing thresholds based on said at least one processed brain signal.

4. A hearing aid according to claim 3 wherein the estimate of the user's hearing threshold is based on said at least one processed brain signal from said at least one low voltage electric signal picked up by said at least one electrode over a period of time, termed the measurement time, longer than 8 hours.

5. A hearing aid according to claim 3 wherein the signal processing unit is configured to run a fitting algorithm to determine appropriate frequency dependent gains for the user from said estimated hearing thresholds.

6. A hearing aid according to claim 5 wherein the signal processing unit is configured to modify presently used frequency dependent gains.

7. A hearing aid according to claim 3 comprising a memory for logging values of said estimated hearing thresholds of the user over time.

8. A hearing aid according to claim 7 wherein the signal processing unit is configured to determine whether said estimated hearing thresholds or a hearing threshold measure derived therefrom change over time.

9. A hearing aid according to claim 8 comprising an alarm indication unit configured to issue an alarm signal to the user in case said estimated hearing thresholds deteriorate over time.

10. A hearing aid according to claim 9 wherein said deterioration includes that said estimated hearing thresholds increase above predetermined relative or absolute levels or that their rates of change are above predefined values.

11. A hearing aid according to claim 1 comprising a user interface configured to allow a user to activate or deactivate a specific mode wherein the voltages or data from the electrodes are recorded for further processing to determine said estimate of the user's hearing thresholds.

12. A hearing aid according to claim 1 configured to determine at least an estimate of real or absolute time elapsed between two time instances where estimates of hearing thresholds of the user are determined and stored.

13. Use of a hearing aid as claimed in claim 1.

14. A method of operating a hearing aid, the hearing aid including
an ear part configured to be mounted fully or partially at an ear or in an ear canal of a user, the ear part including a housing, and
at least one electrode located at a surface of said housing to allow said at least one electrode to contact the skin of a user when said ear part is operationally mounted on the user, and configured to pick up at least one low voltage electric signal from the user's brain; and
an amplifier unit operationally connected to said at least one electrode and configured to amplify said at least one low voltage electric signal to provide at least one amplified brain signal;
an input transducer for providing an electric audio input signal;
an output transducer for converting an electric output signal to an acoustic output sound to the user;
a signal generator for generating an electric test signal, the signal generator being operationally connected to said output transducer allowing said electric test signal to be presented to a user as an auditory test stimulus; and
a signal processing unit, said signal processing unit being operationally connected
to said amplifier unit,
to said input transducer, and
to said output transducer,
the method comprising:
mounting said hearing aid on said user;
applying a time and frequency dependent gain to said electric audio input signal or a signal originating therefrom and providing a processed audio output signal;
generating and specifically adapting said electric test signal to be presented to the user as an auditory test stimulus and used in an auditory evoked potential measurement;
mixing said processed audio output signal or a signal originating therefrom and said electric test signal to said electric output signal for being presented together to the user as said acoustic output sound wherein said electric output signal is converted to said acoustic output sound during normal daily life use of the hearing aid; and
recording and processing said at least one amplified brain signal to provide at least one processed brain signal.

15. A method according to claim 14 further comprising that the user's hearing thresholds are estimated based on said at least one processed brain signal.

16. A method according to claim 15 wherein the estimate of the user's hearing threshold is based on said at least one processed brain signal from said at least one low voltage electric signal picked up by said at least one electrode over a period of time, termed the measurement time, longer than 8 hours.

17. A method according to claim 15 further comprising running a fitting algorithm using said estimated hearing thresholds to determine appropriate frequency dependent gain for the user.

18. A method according to claim 17 comprising that the currently used frequency dependent gain is modified based on said estimated hearing thresholds.

19. A method according to claim 14 wherein the measurement of auditory evoked potentials is selected among Auditory Brainstem Response, including Auditory Brainstem Responses to complex sounds, Auditory Steady State Response, and Frequency Following Response.

20. A data processing system comprising a processor and program code means for causing the processor to perform the steps of the method of claim 14.

* * * * *